United States Patent
Smeets et al.

(10) Patent No.: US 7,358,357 B2
(45) Date of Patent: Apr. 15, 2008

(54) PROCESS FOR PREPARING CAPROLACTAM BY ADMIXTURE OF CYCLOHEXANONE OXIME TO A REACTION MIXTURE UNDER TURBULENT FLOW CONDITIONS

(75) Inventors: Theodorus Maria T. M. Smeets, Elsloo (NL); Joannes Albertus Wihelmus J. A. W. Lemmens, Roermond (NL); Frank F. Mostert, Maastricht (NL); Peter Wei-Hae P. W-H. Cheng, Augusta, GA (US)

(73) Assignee: DSM IP Assets B.V., Heerlen (NL)

( * ) Notice: Subject to any disclaimer, the term of this patent is extended or adjusted under 35 U.S.C. 154(b) by 188 days.

(21) Appl. No.: 10/557,770

(22) PCT Filed: May 17, 2004

(86) PCT No.: PCT/EP2004/005338

§ 371 (c)(1),
(2), (4) Date: Nov. 21, 2005

(87) PCT Pub. No.: WO2004/013287

PCT Pub. Date: Dec. 29, 2004

(65) Prior Publication Data

US 2007/0060749 A1    Mar. 15, 2007

(30) Foreign Application Priority Data

| May 23, 2003 | (EP) | 03076589 |
| May 23, 2003 | (EP) | 03076590 |
| May 23, 2003 | (EP) | 03076591 |
| May 23, 2003 | (EP) | 03076592 |

(51) Int. Cl.
*C07D 223/10* (2006.01)
(52) U.S. Cl. ..................... 540/535
(58) Field of Classification Search .............. 540/535
See application file for complete search history.

(56) References Cited

U.S. PATENT DOCUMENTS

| 3,553,204 A | 1/1971 | Gehring et al. |
| 3,914,217 A | 10/1975 | Smith |
| 7,141,668 B2 | 11/2006 | Smeets et al. |

FOREIGN PATENT DOCUMENTS

| GB | 1105805 | 3/1968 |
| GB | 1 240 756 | 7/1971 |
| GB | 1 581 788 | 12/1990 |

OTHER PUBLICATIONS

Lemmens et al, U.S. Appl. No. 10/557,753, filed Nov. 21, 2005.
Thomissen et al, U.S. Appl. No. 10/557,771, filed Nov. 29, 2006.
Smeets et al, U.S. Appl. No. 10/565,774, filed Sep. 6, 2006.

*Primary Examiner*—Bruck Kifle
(74) *Attorney, Agent, or Firm*—Nixon & Vanderhye P.C.

(57) ABSTRACT

The invention relates to a process for preparing caprolactam by admixture of cyclohexanone oxime to a reaction mixture comprising caprolactam and sulfuric acid using a mixing device, said mixing device comprising (i) a tube through which the reaction mixture can flow, and (ii) channels disposed around the tube, said channels opening into the tube, said process comprising: passing the reaction mixture through the tube, and feeding the cyclohexanone oxime into the reaction mixture through one or more of said channels, wherein Re>5000, Re being the Reynolds number as defined by $\rho \cdot V \cdot D/\eta$, wherein $\rho$=density (in $kg/m^3$) of the reaction mixture that is fed to the tube $V$=velocity of the reaction mixture, V being defined as W/A, wherein W is the flow rate (in $m^3/s$) of the reaction mixture that is fed into the tube and A is the cross section area of the tube (in $m^2$) at the level where said channels open into the tube $D$=diameter of the tube at the level where said channels open into the tube (in m)

Figure 1:
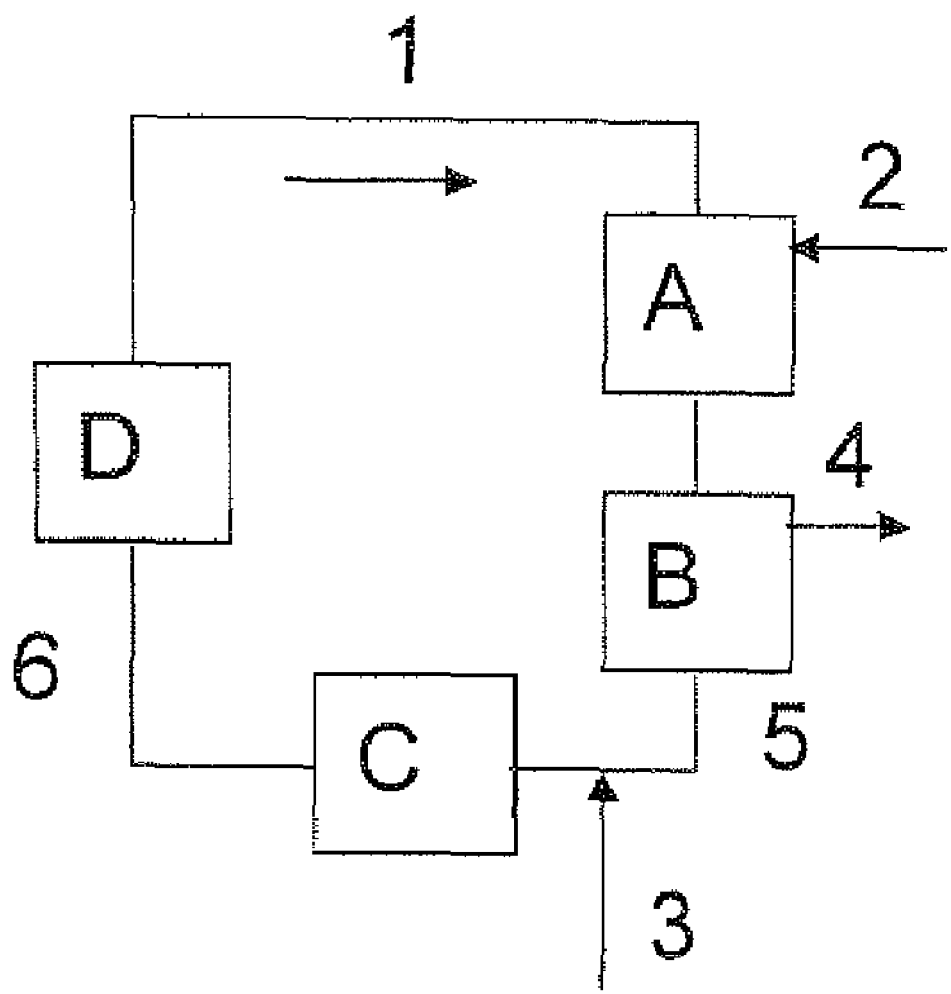

$\eta$=viscosity of the reaction mixture that is fed into the tube (in Pa·s).

14 Claims, 3 Drawing Sheets

PROCESS FOR PREPARING CAPROLACTAM BY ADMIXTURE OF CYCLOHEXANONE OXIME TO A REACTION MIXTURE UNDER TURBULENT FLOW CONDITIONS

The invention relates to a process and an apparatus for preparing caprolactam by admixture of cyclohexanone oxime to a reaction mixture comprising caprolactam, sulfuric acid and optionally free $SO_3$.

Caprolactam can be prepared by Beckmann rearrangement of cyclohexanone oxime. Such Beckmann rearrangement can be carried out by admixing cyclohexanone oxime to a reaction mixture comprising caprolactam, sulfuric acid and optionally free $SO_3$. In such process the sulfuric acid and optional free $SO_3$ catalyse the conversion of cyclohexanone oxime towards caprolactam.

U.S. Pat. No. 3,601,318 describes the importance of the mixing conditions to obtain caprolactam of the desired purity. A mixing device is disclosed comprising a tube through which a process liquid can flow, which tube, as seen in the direction of flow, narrows to a throat, and which beyond the throat widens. A plurality of channels is disposed around the tube and open into the tube, through which channels a feed liquid can be admixed to the process liquid. It is described that the mixing device is particularly suited for situations wherein the liquids must be thoroughly and completely mixed in the virtual absence of any turbulence. One of such situations is described to be the Beckmann rearrangement of cyclic ketoximes in the presence of sulfuric acid or phosphoric or polyphosphoric acids.

We found that the use of the mixing device as prescribed in U.S. Pat. No. 3,601,318, i.e. under conditions of laminar flow, for the preparation of caprolactam results in a low yield.

Goal of the invention is to improve the yield.

This goal is achieved according to the invention by providing a process for preparing caprolactam by admixture of cyclohexanone oxime to a reaction mixture comprising caprolactam and sulfuric acid using a mixing device, said mixing device comprising (i) a tube through which the reaction mixture can flow, and (ii) channels disposed around the tube, said channels opening into the tube, said process comprising: passing the reaction mixture through the tube, and feeding the cyclohexanone oxime into the reaction mixture through one or more of said channels, wherein Re>5000, Re being the Reynolds number as defined by $\rho \cdot V \cdot D / \eta$, wherein $\rho$=density (in kg/m$^3$) of the reaction mixture that is fed to the tube V=velocity of the reaction mixture, V being defined as W/A, wherein W is the flow rate (in m$^3$/s) of the reaction mixture that is fed into the tube and A is the cross section area of the tube (in m$^2$) at the level where said channels open into the tube.

D=diameter of the tube at the level where said channels open into the tube (in m).

$\eta$=viscosity of the reaction mixture that is fed into the tube (in Pa·s).

It was found that the yield is increased when the increased Reynolds number is applied according to the invention. Moreover, a high purity is achieved.

This process is distinguished from the process of U.S. Pat. No. 3,601,318 in that the main stream of U.S. Pat. No. 3,601,318 is in laminar flow. The Reynolds number corresponding a laminar flow is not higher than 2100.

According to the invention Re>5.000. A further increase of the yield is advantageously achieved applying increased values of Re. Preferably, Re>10.000, more preferably >15.000, more preferably >20.000, more preferably >25.000. For practical reasons, Re is generally <100.000.

Desired values for Re according to the invention can advantageously be achieved by selecting a suitable combination of $\rho$, V, D, and $\eta$.

According to the invention, the reaction mixture is passed through a tube. Any suitable tube may be used through which a liquid may be passed. Preferably, the tube has a generally cylindrical shape. Preferably, the tube, as seen in the direction of flow, narrows, in a first part, to a throat, and, optionally, widens beyond the throat in a second part. Preferably, the channels open into the first part, the throat or the second part of the tube, most preferably into the throat. As used herein the throat refers to the part of the tube beyond the first part (seen in the direction of flow) having the smallest cross section area. The angle with which the first part narrows (angle between the wall of the first part and the axis of the tube) is preferably more than 5°. The angle with which the second part widens is preferably more than 5° (angle between the wall of the second part and the axis of the tube).

According to the invention, channels are disposed around the tube. The channels may be any suitable openings through which cyclohexanone oxime can be fed into the reaction mixture. The channels may have any suitable diameter. The diameter of the channels is preferably at least 2 mm. This reduces the risk of clogging of the channels. The number of channels that are disposed around the tube may vary, and may for instance be between 2 and 32, preferably between 4 and 24. Preferably, the mixing device comprises a feed chamber, said feed chamber being disposed around the tube, from which feed chamber the channels open into the tube. The feed chamber may be connected to the source of cyclohexanone oxime, and cyclohexanone oxime may be fed from the feed chamber, through the channels into the tube.

According to the invention cyclohexanone oxime is fed into the reaction mixture comprising caprolactam, sulfuric acid and optionally $SO_3$. As a result cyclohexanone oxime is converted into caprolactam by Beckmann rearrangement. Such conversion is known to occur almost instantaneously.

The reaction mixture comprises caprolactam, sulfuric acid and optionally $SO_3$. Preferably, the ratio M defined as $(n_{SO3}+n_{H2SO4})/n_{cap}$ is between 1 and 2.2, more preferably between 1.1 and 1.9, wherein $n_{SO3}$=quantity of $SO_3$ in reaction mixture (in mol), $n_{H2SO4}$=quantity of $H_2SO_4$ in the reaction mixture (in mol), $n_{cap}$=quantity of caprolactam in reaction mixture (in mol). The reaction mixture preferably comprises $SO_3$, the $SO_3$ content preferably being at least 1 wt. %, more preferably at least 2 wt. %, more preferably at least 4 wt. % $SO_3$, more preferably at least 6 wt. % $SO_3$, more preferably at least 8 wt % $SO_3$, more preferably at least 10 wt. % $SO_3$, more preferably at least 12 wt. % $SO_3$. For practical reasons, the $SO_3$ content of the reaction mixture is usually less than 20 wt. %, for instance less than 18 wt. %, for instance less than 17 wt. %. As used herein the $SO_3$ content refers to the weight of the $SO_3$ relative to the weight of the reaction mixture. In a preferred embodiment M is between 1.0 and 1.4, preferably between 1.15 and 1.4, the $SO_3$ content of the reaction mixture being at least 2 wt. % $SO_3$, more preferably at least 4 wt. % $SO_3$, more preferably at least 6 wt. % $SO_3$, more preferably at least 8 wt % $SO_3$, more preferably at least 10 wt. % $SO_3$, more preferably at least 11 wt. % $SO_3$. A value for M of between 1.0 and 1.4, preferably between 1.15 and 1.4, in combination with increased values for the $SO_3$ content has the advantage that relatively low quantities of ammonium sulfate are formed during a subsequent neutralization, while the yield is found to increase with increased $SO_3$ content. As used herein the values for M and the concentrations $SO_3$ and the temperature of the reaction mixture refer in particular to the values in the reaction mixture obtained after feeding of the cyclohexanone oxime into the reaction mixture, in particular of the reaction mixture leaving the mixing device.

The values for M and the $SO_3$ content may be obtained in any suitable way. In a preferred embodiment, the process is a continuous process comprising keeping the reaction mixture in circulation, feeding a mixture comprising sulfuric acid and $SO_3$, for instance oleum or a reaction mixture comprising caprolactam, sulfuric acid and $SO_3$ to the circulating reaction mixture, and withdrawing part of the circulating reaction mixture. The amount of mixture comprising sulfuric acid and $SO_3$, the $SO_3$ content thereof and the amount of cyclohexanone oxime fed to the circulating reaction mixture may be chosen such that M and the $SO_3$ content of the reaction mixture have the preferred values. Oleum may have any suitable $SO_3$ concentration, for instance 18 to 35 wt. % $SO_3$.

The temperature in the reaction mixture may have any suitable value. Preferably, the temperature in the reaction mixture is between 50 and 130° C., preferably between 70 and 120° C.

The flow rate of reaction mixture that is fed to the tube and the flow rate of the cyclohexanone oxime that is fed into the reaction mixture may have any suitable value. Preferably, the ratio w/W<0.1, preferably, w/W<0.05, wherein, w=flow rate (in $m^3/s$) of the cyclohexanone oxime which is fed into the reaction mixture through said one ore more channels, and W=flow rate (in $m^3/s$) of the reaction mixture which is passed through the tube. Using low values for the ratio w/W was found to result in improved yield and purity. Advantageously, w/W<0.04, preferably w/W<0.03. There is no specific lower limit for w/W. In practice, w/W may be >0.01.

The velocity of the cyclohehexanone oxime that is fed into the reaction mixture and the reaction mixture may have any suitable value. Preferably, v/V is between 0.1 and 30, wherein v=the velocity (in m/s) at which cyclohexanone oxime is fed into the reaction mixture, V=velocity of the reaction mixture at the level where said channels open into the tube, V being defined as W/A, wherein W is the flow rate (in $m^3/s$) of the reaction mixture that is fed into the tube and A is the cross section area of the tube (in $m^2$) at the level where said channels open into the tube. The ratio v/V may be <15, for instance <10, for instance <5, for instance <2, for instance <1.8, for instance <1.5. The ratio v/V may be >0.2, for instance >0.5.

Preferred values for v/V can be selected in any suitable way. In a preferred embodiment, the mixing device comprises one ore more closures, one or more of the channels being closable with a closure. Preferably each of the channels is closable with a closure. As closure can be used any suitable closure means with which a channel can be closed and opened, for instance a plug. Preferably a closure or plug is used having a tip complimentary in shape to the channel. Preferably, the closures or plugs have a tip complimentary in shape to the channels. This is an effective way of closing a channel.

In a preferred embodiment a circulation system is provided comprising (i) the mixing device, (ii) a cooler for cooling the reaction mixture, (iii) a connecting circuit through which the reaction mixture can flow from the mixing device to the cooler, and from the cooler back to the mixing device, the process comprising circulating the reaction mixture from the mixing device to the cooler and from the cooler back to the mixing device. The reaction mixture may be kept in circulation in any suitable way. Preferably, the circulation system comprises (iv) a pump for keeping the reaction mixture in circulation. Preferably, the pump is downstream of the mixing device and upstream of the cooler, as seen in the direction of flow of the reaction mixture. This arrangement is found to facilitate achieving a high Reynolds number.

In a preferred embodiment, the process comprises collecting the reaction mixture leaving the tube in a collecting vessel. In the collecting vessel additional conversion of cyclohexanone oxime may take place, if not all cyclohexanone oxime would have been converted. Preferably, a collecting vessel is provided arranged to receive the reaction mixture leaving the tube; and the process comprises collecting the reaction mixture leaving the tube in the collecting vessel. Preferably, the circulation system comprises the collecting vessel, the collecting vessel preferably being upstream of the pump, as seen in the direction of flow of the reaction mixture. This is found to facilitate achieving a high Reynolds number.

In a preferred embodiment, the mixing device comprises adjustable closures, the tube being conducted through the wall of the collecting vessel at a point downstream of the closures as seen in the direction of flow of the reaction mixture. In this embodiment the advantages of the collecting vessel are achieved, while it is still possible to operate the closures in a simple way. Therefore, in another aspect the invention also provides an apparatus, said apparatus comprising (a) a mixing device, said mixing device comprising (i) a tube through which a first liquid can flow (ii) channels disposed around the tube, through which channels a second liquid can be added to the first liquid, said channels opening into the tube (iii) adjustable closures associated with one or more of the channels; and (b) a collecting vessel for collecting the first liquid leaving the tube, said collecting vessel having a wall, wherein the tube is conducted through the wall of the collecting vessel at a point downstream of the closures as seen in the direction of flow of the reaction mixture.

The tube may comprise a third part beyond the second part as seen in the direction of flow, said third part being connected to the second part, the process comprising the reaction mixture that leaves the second part of the tube through the third part of the tube.

The process according to the invention is preferably a continuous process.

In a preferred embodiment, the process comprises a) feeding (i) oleum and (ii) cyclohexanone oxime into a first reaction mixture comprising caprolactam, sulfuric acid and $SO_3$; and b) feeding (iii) a portion of the first reaction mixture and (iv) cyclohexanone oxime into a second reaction mixture comprising caprolactam, sulfuric acid and $SO_3$, wherein said feeding of said cyclohexanone oxime into the first reaction mixture and said feeding of said cyclohexanone oxime into the second reaction mixture is carried out according to the process according to the invention. In a further preferred embodiment, the process further comprises feeding (v) a portion of the second reaction mixture and (vi) cyclohexanone oxime into a third reaction mixture comprising caprolactam, sulfuric acid and $SO_3$, and wherein said feeding of said cyclohexanone oxime into the third reaction mixture is carried out according to the invention.

Preferably, the first reaction mixture, the second reaction mixture and/or said third reaction mixture are kept in circulation.

The first reaction mixture, the second reaction mixture, and the optional third reaction mixture comprise caprolactam, sulfuric acid and $SO_3$. The molar ratio M defined as $(n_{SO3}+n_{H2SO4})/n_{cap}$, wherein $n_{SO3}$=quantity of $SO_3$ in reaction mixture, in mol, $n_{H2SO4}$=quantity of $H_2SO_4$ in reaction mixture, in mol, and $n_{cap}$=quantity of caprolactam in reaction mixture, in mol, is preferably different in each reaction mixture. The molar ratio M in the first, second and third reaction mixture will, as used herein, be referred to as M(1), M(2) and M(3) respectively. The concentration $SO_3$ in the first, second, and third reaction mixture will, as used herein, be referred to as $C_{SO3}(1)$, $C_{SO3}(2)$ and $C_{SO3}(3)$. As used herein the $SO_3$ concentration will be given in wt. % relative to the weight of the reaction mixture. The temperature in the first, second and third reaction mixture will, as used herein, be referred to as T(1), T(2) and T(3) respectively. As used herein, the values for M, the $SO_3$ concentration, and the temperature refer in particular to the value in the reaction mixture obtained after feeding of the cyclohexanone oxime into the reaction mixture, in particular in the reaction mixture leaving the mixing device.

Preferred values for M and the $SO_3$ concentration can be obtained by feeding cyclohexanone oxime to the different stages in the appropriate amounts, and by applying appropriate quantities of oleum of appropriate $SO_3$ concentration.

Preferably, M(2) is lower than M(1). Preferably M(3) is lower than M(2).

In a preferred embodiment, M(1) is between 1.2 and 2.2, preferably between 1.4 and 1.85, more preferably between 1.5 and 1.7. Preferably, $C_{SO3}(1)$ is between 3 and 20 wt. %, preferably higher than 4 wt. %, preferably higher than 6 wt. %, more preferably higher than 8 wt. %; more preferably higher than 10 wt. %, more preferably higher than 12 wt. %. Increased values for $C_{SO3}(1)$ have the advantage that $C_{SO3}(2)$ can be kept high in the second reaction mixture without having to feed oleum to the second reaction mixture. $C_{SO3}(1)$ may be less than 18 wt. %, preferably less than 17 wt. %. Preferably T(1) is between 50 and 130° C., preferably between 70 and 130° C., more preferably between 70 and 120° C.

In a preferred embodiment M(2) is between 1.0 and 1.6, preferably higher than 1.1, more preferably higher than 1.2, preferably less than 1.5, more preferably less than 1.4. Preferably, $C_{SO3}(2)$ is between 0.5 and 20 wt. %, more preferably higher than 1 wt. %, more preferably higher than 2 wt. %, more preferably higher than 4 wt. %, more preferably higher than 6 wt. %, more preferably higher than 8 wt. %, more preferably higher than 10 wt. %, more preferably higher than 12 wt. %. Increased concentrations of $C_{SO3}(2)$ within the abovementioned ranges for M(2) were surprisingly found to result in significantly higher yields. Preferably T(2) is between 70 and 130° C., preferably between 80 and 130° C., more preferably between 80 and 120° C.

In a preferred embodiment M(3) is between 1.0 and 1.4, preferably between 1.1 and 1.35, more preferably between 1.15 and 1.35. Preferably, $C_{SO3}(3)$ is between 0.5 and 18 wt. %, preferably higher than 1 wt. %, preferably higher than 2 wt. %, more preferably higher than 4 wt. %, preferably higher than 6 wt. %, more preferably higher than 8 wt. %, more preferably higher than 10 wt. %, more preferably higher than 12 wt. %. Increased concentrations of $C_{SO3}(2)$ within the abovementioned ranges for M(3) were surprisingly found to result in significantly higher yields. Preferably T(3) is between 70 and 130° C., preferably between 80 and 130° C., more preferably between 80 and 120° C.

Oleum may be fed into a reaction mixture in any suitable way. Preferably all oleum applied is fed into the first reaction mixture. Preferably, the amount of cyclohexanone oxime fed to the first reaction mixture is larger than the amount of cyclohexanone oxime fed to the second reaction mixture, and, if applicable, preferably the amount of cyclohexanone oxime fed to the second reaction mixture is larger than the amount of cyclohexanone oxime fed to the third reaction mixture. Preferably, from 60 to 95 wt. % of the total amount of cyclohexanone oxime fed into the first, second and, if applicable, third reaction mixture, is fed into the first reaction mixture. Preferably, from 5 to 40 wt. % of the total amount of cyclohexanone oxime fed into the first, second and, if applicable, third reaction mixture is fed into the second reaction mixture. If applicable, preferably, from 2 to 15 wt. % of the total amount of cyclohexanone oxime fed into the first, second and third reaction mixture is fed into the third reaction mixture.

Preferably, one parts by volume of cyclohexanone oxime is continuously introduced into at least 10 parts by volume, more preferably at least 20 parts by volume of reaction mixture.

Preferably, w1/W1<0.01, preferably w1/W1<0.05. Preferably, w2/W2<0.01, preferably w2/W2<0.05, Preferably, w3/W3<0.01, preferably w3/W3<0.05, wherein w1, w2, w3=flow rate (in m³/s) of the cyclohexanone oxime which is fed through said one ore more first channels, second channels and third channels, respectively; and W1, W2, W3=flow rate (in m³/s) of the reaction mixture which is passed through the first tube, second tube and third tube respectively.

A continuous process according to the invention preferably involves feeding a portion of the first reaction mixture into the second reaction mixture. A continuous process according to the invention preferably involves withdrawing a portion of the second reaction mixture. A continuous process according to the invention may involve feeding a portion of the second reaction mixture into the third reaction mixture. A continuous process according to the invention may involve withdrawing a portion from the third reaction mixture.

A portion of the second reaction mixture and/or of the third reaction mixture may be withdrawn in any suitable way. Caprolactam may be recovered from the second or third reaction mixture by known methods, for instance by neutralization with ammonia, and purification of the caprolactam-containing aqueous phase obtained.

According to the invention cyclohexanone oxime is fed into the reaction mixture. The cyclohexanone oxime that is fed to the reaction mixture may comprise water, for instance less than 7 wt. %. Preferably, the cyclohexanone oxime that is fed into the reaction mixture has a water content of less than 2 wt. %, more preferably less than 1 wt. %, more preferably less than 0.2 wt. %, more preferably less than 0.1 wt. %. Feeding cyclohexanone oxime having a low water content is advantageous as it is an effective way for achieving a reaction mixture having high $SO_3$ content.

One way of obtaining cyclohexanone oxime having a water content of less than 2 wt. % is drying cyclohexanone oxime with a high water content for example with inert gas.

A preferred way of obtaining cyclohexanone oxime having a water content of less than 2 wt. % is a process in which cyclohexanone oxime is obtained by a) preparing an organic medium comprising cyclohexanone oxime dissolved in an organic solvent, and
b) separating, by distillation, cyclohexanone oxime from said organic medium.

Preparing an organic medium comprising cyclohexanone oxime dissolved in an organic solvent is preferably carried out by contacting in a reaction zone in countercurrent flow a stream of a solution of cyclohexanone in an organic solvent which is also a solvent for the cyclohexanone oxime and a stream of an a phosphate buffered, aqueous solution of hydroxylammonium; and withdrawing from the reaction zone an organic medium of cyclohexanone oxime dissolved in said organic solvent. Particularly suitable organic solvent for use in the process for preparing cyclohexanone oxime are toluene and benzene. Preferably toluene is used as organic solvent. The phosphate buffered, aqueous reaction medium is preferably continuously recycled between a hydroxylammonium synthesis zone and a cyclohexanone oxime synthesis zone. In the hydroxylammonium synthesis zone hydroxylammonium is formed by catalytic reduction of nitrate ions or nitric oxide with hydrogen. In the cyclohexanone oxime synthesis zone, hydroxylammonium formed in the hydroxylammonium synthesis zone reacts with cyclohexanone to form cyclohexanone oxime. The cyclohexanone oxime can then be separated from the aqueous reaction medium which is recycled to the hydroxylammonium synthesis zone. An organic medium comprising the formed cyclohexanone oxime dissolved in said organic solvent is withdrawn from the reaction zone, and distilled to recover cyclohexanone oxime having a water content less than 1 wt. % and even less than 0.1 wt. %.

The recovery of caprolactam from the reaction mixture obtained may be performed by known methods. Preferably, the reaction mixture obtained in the last stage of the Beckmann rearrangement is neutralized with ammonia in water and the ammonium sulfate thus formed is removed from the caprolactam solution. The caprolactam solution may be purified by known procedures.

The invention also provides an apparatus for carrying out the process according to the invention, said apparatus comprising a mixing device for admixing cyclohexanone oxime to the reaction mixture, said mixing device comprising (i) a tube through which the reaction mixture can flow (ii) channels disposed around the tube through which channels cyclohexanone oxime can be fed into the reaction mixture, said channels opening into the tube; a cooler for cooling the reaction mixture: a pump; and a connecting circuit through which the reaction mixture leaving the mixing device can flow from the mixing device to the pump, from the pump to the cooler (D), and from the cooler back to mixing device. It was found that when the pump is downstream of the mixing device and upstream of the cooler, the Reynolds number according to the invention are advantageously achieved.

The invention also provides an apparatus according for carrying out the process according to the invention, said apparatus comprising:

a mixing device for admixing cyclohbxanone oxime to the reaction mixture, said mixing device comprising (i) a tube through which the reaction mixture can flow (ii) channels disposed around the tube through which channels cyclohexanone oxime can be fed into the reaction mixture, said channels opening into the tube; a collecting vessel a cooler for cooling the reaction mixture; a connecting circuit through which the reaction mixture can flow from the mixing device; to the collecting vessel, from collecting vessel to cooler, and from cooler to the mixing device. It was found that, in particular when the that the outlet for the reaction mixture that is passed through the connecting circuit to the cooler, is in the lower part of the collecting vessel, e.g. below 50% of the height of the collecting vessel, the Reynolds number according to the invention is advantageously achieved.

In a preferred embodiment, the mixing device preferably one or more closures, one or more of the channels being closable with a closure, and the tube extends through the wall of the collecting vessel, such that the closures are still outside the collecting vessel. This facilitates the use of the closures.

Preferably, the tube, as seen in the direction of flow, narrows, in a first part, to a throat, and the tube, optionally, widens beyond the throat in a second part. This also facilitates achieving a high Reynolds number according to the invention.

In another aspect the invention also provides an apparatus for preparing caprolactam, said apparatus comprising:

a) a first circulation system for keeping a first reaction mixture in circulation, said first circulation system comprising a first mixing device for admixing cyclohexanone oxime to the first reaction mixture, said first mixing device comprising:
   (a1) a first tube through which the first reaction mixture can flow;
   (a2) first channels disposed around the first tube through which first channels cyclohexanone oxime can be fed into the first reaction mixture, said first channels opening into the first tube; and
   (a3) one or more first closures, one or more of the first channels being closable with a first closure; and
b) a second circulation system for keeping a second reaction mixture in circulation, said second circulation system comprising a second mixing device for admixing cyclohexanone oxime to the second reaction mixture, said second mixing device comprising:
   (b1) a second tube through which the second reaction mixture can flow;
   (b2) second channels disposed around the second tube through which second channels cyclohexanone oxime can be fed into the second reaction mixture, said second channels opening into the second tube; and
   (b3) one or more second closures, one or more of the second channels being closable with a second closure.

This apparatus it a preferred embodiment for allowing the mixing conditions to be selected per stage.

In a preferred embodiment, the apparatus further comprises:
c) a third circulation system for keeping a third reaction mixture in circulation, said third circulation system comprising a third mixing device for admixing cyclohexanone oxime to the third reaction mixture, said third mixing device comprising:
   (c1) a third tube through which the third reaction mixture can flow;
   (c2) third channels disposed around the third tube through which third channels cyclohexanone oxime can be fed into the third reaction mixture, said third channels opening into the third tube; and
   (c3) one or more third closures, one or more of the third channels being closable with a third closure.

Further preferred embodiments for the apparatus are described in the entire specification and in the claims.

In another aspect the invention also provides a process for preparing caprolactam, said process comprising:

a) passing a first reaction mixture through the first tube, and keeping the first reaction mixture in circulation, said first reaction mixture comprising caprolactam, sulfuric acid and $SO_3$;
b) feeding cyclohexanone oxime into the first reaction mixture through the first openings.
c) passing a second reaction mixture through the second tube, and keeping the second reaction mixture in circulation, said second reaction mixture comprising caprolactam, sulfuric acid and free $SO_3$;
d) feeding into the second reaction mixture cyclohexanone oxime and a portion of the first reaction mixture, said cyclohexanone oxime being fed into the second reaction mixture through the second openings.

Preferably the process comprises the process comprises:

e) passing a third reaction mixture through the third tube, and keeping the third reaction mixture in circulation, said third reaction mixture comprising caprolactam, sulfuric acid and free $SO_3$;

Further preferred embodiments of the process according to the invention are described in the entire specification and in the claims.

DESCRIPTION OF A PREFERRED EMBODIMENT

FIG. 1 shows a preferred embodiment for carrying out the process according to the invention.

Referring to FIG. 1, reaction mixture is kept in circulation in the direction of the arrow in a circulation system comprising mixing device A, collecting vessel B, pump C and cooler D. Mixing device A comprises the tube that opens into collecting vessel B. To mixing device A are fed the reaction mixture via line 1 and cyclohexanone oxime via line 2. The reaction mixture leaving mixing device A is collected in collecting vessel B. Part of the reaction mixture is withdrawn from collecting vessel B via line 4. Another part of the reaction mixture is withdrawn from collecting vessel B via line 5, and, together with oleum (or a reaction mixture that is withdrawn from another circulation system) that is supplied via line 3, fed to pump C. The reaction mixture leaving pump C enters cooler D via line 6, and is recycled to mixing device A via line 1.

Figure 2:
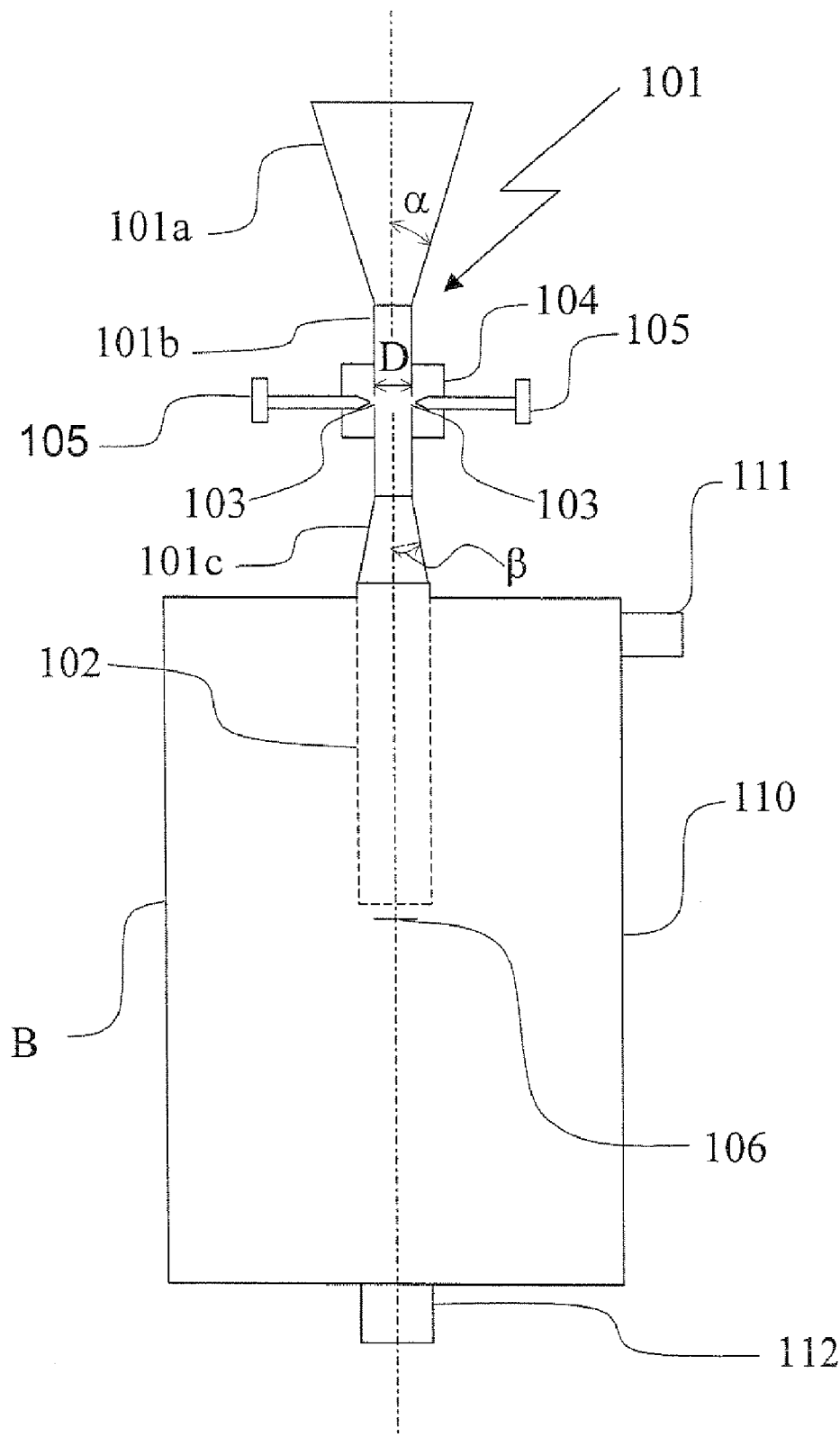

FIG. 2 shows a preferred embodiment for the mixing device.

Mixing device A, as illustrated in FIG. 2, comprises a cylindrical tube 101 that in first part 101a narrows to throat 101b having a diameter D as is used in the calculation of the Reynolds number, and beyond throat 101b widens in a second part 101c. The second part 101c of the tube is connected to third part 102. Channels 103, which are in connection with feed chamber 103, open into tube 101. Cyclohexanone oxime is supplied via feed chamber 103, and fed into reaction mixture through channels 103. The mixing device comprises closures 105 with which channels 103 can be opened and closed independently.

The tube opens into collecting vessel B, having walls 110. The mixing device optionally also comprises a baffle 106 opposite to the exit of tube 101. Outlets 111 and 112, respectively, correspond to the connections to lines 4 and 5 shown in FIG. 1.

Figure 3:
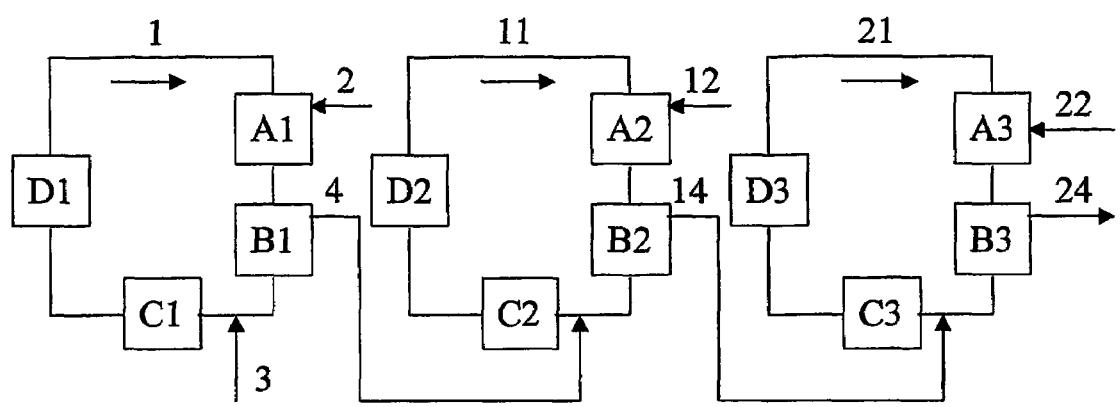

FIG. 3 shows a preferred set-up for a rearrangement in three stages comprising a first circulation system, a second circulation system and a third circulation system. The first circulation system comprises mixing device A1, collecting vessel B1, pump C1 and cooler D1, and a first reaction mixture is kept in circulation via line 1. The second circulation system comprises mixing device A2, collecting vessel B2, pump C2 and cooler D2, and a second reaction mixture is kept in circulation via line 11. The third circulation system comprises mixing device A3, collecting vessel B3, pump C3 and cooler D3, and a third reaction mixture is kept in circulation via line 21. Cyclohexanone oxime and oleum are fed into the first reaction mixture via line 2 and line 3, respectively. A portion of the first reaction mixture is withdrawn from collecting vessel B1 via line 4 and fed into the second reaction mixture. Cyclohexanone oxime is fed into the second reaction mixture via line 12. A portion of the second reaction mixture is withdrawn from collecting vessel B2 via line 14 and fed into the third reaction mixture. Cyclohexanone oxime is fed to the third reaction mixture via line 22. A portion of the third reaction mixture is withdrawn form collecting vessel B3 via line 24. The process is carried out continuously.

The following specific examples are to be construed as merely illustrative, and not limitative, of the remainder of the disclosure.

COMPARATIVE EXPERIMENT AND EXAMPLES

In the comparative experiment and the example the yield to caprolactam (amount of caprolactam formed per amount of cyclohexanone oxime fed to the reaction mixture) was determined as follows. Samples were taken at outlet 111. To a first part (0.2 g) of each sample concentrated sulfuric acid (20 ml, 96 wt %) was added, as well as 15 g $K_2SO_4$ and 0.7 HgO. The nitrogen content of the resulting acidic mixture was determined using the Kjeldahl Method, from which the molar concentration of nitrogen in the first part of the sample (TN) was calculated. A second part of each sample is extracted with chloroform. This method is based on the fact that caprolactam enters the chloroform phase. The impurities stay in the water phase. The extracted aqueous phase is analyzed for its nitrogen content by the Kjeldahl Method, from which the molar concentration of nitrogen in the second part of the sample (RN) was calculated. The yield is calculated as follows:

$$\% \text{ yield} = \left(1 - \frac{RN}{TN}\right) \times 100$$

The adsorbance at 290 nm ($E_{290}$ nm), used as quality specification of the obtained caprolactam, was determined as follows:

The reaction mixture leaving outlet 111 was neutralized with ammonia, and the resulting caprolactam-containing aqueous phase was separated. The absorbance of the separated caprolactam-containing aqueous phase was measured at a wavelength of 290 nm using a 1 cm cuvet (calculated for a 70 wt. % caprolactam solution)

Comparative Experiment A

A set-up was used as depicted in FIGS. 1 and 2. The mixing device had the following dimensions: diameter pipe prior to the narrowing 101a: 2600 mm, angle α: 17°, diameter throat 101b: 100 mm, angle β: 11°. Baffle 106 was not applied. The circulating reaction mixture contained 7 wt. % $SO_3$, M being 1.6 (measured in collecting vessel B). The viscosity of the reaction mixture fed to the mixer was 0.18 Pa·s, the density being 1400 kg/m³. The temperature in the collecting vessel was 115° C. The temperature in the reaction mixture leaving the cooler and fed into the mixer was 75° C. The flow rate of the reaction mixture was 73 m³ per hour, corresponding to a velocity of 2.5 m/s. The resulting Reynolds number in the throat is 2000. The mixing device was provided with 12 channels (diameter 3 mm). Cyclohexanone oxime was fed through 3 channels (9 of the channels being in closed position). The flow rate of the cyclohexanone oxime was 3 ton/hr (ρ=850 kg/m³).

The yield was 95 wt. %. The $E_{290}$ was 6.3.

Example 1

Comparative experiment A was repeated with the difference, that the throat of the mixing device had a diameter of 51 mm. The other dimensions of the mixer, including angle α: 17° and angle β: 11° were kept the same. The flow rate of the reaction mixture was 82 m³ per hour, corresponding to a velocity of 11.4 m/s. The temperature in the reaction mixture leaving the cooler and fed into the mixer was 82° C. (viscosity 0.12 Pa·s). The Reynolds number is 6800. The yield was determined to be 96.7%. the $E_{290}$ was 3.3. This example shows that an increase of the Reynolds number from 2000 to 6800 results in an increased yield and an increased purity.

Example 2

Example 1 was repeated with the difference that the flow rate of the reaction mixture was increased from 83 m³/s to 300 m³/s, and that cyclohexanone oxime was fed through 8 channels (4 of the channels being in closed position), the flow rate of the cyclohexanone oxime being 8 ton/hr. The cooling was arranged such that the temperature in collecting vessel remained 115° C. The resulting velocity of the reaction mixture in the throat was 41 m/s, corresponding to a Reynolds number of 29200. The yield was determined to be 99.5%. The $E_{290}$ was 0.43. This example shows that a further increase of the Reynolds number from 6800 to 29200 results in an increased yield and an increased purity.

Table 1 gives an overview of the results.

TABLE 1

| | Re | V | v | v/V | yield | $E_{290}$ |
|---|---|---|---|---|---|---|
| Comp. A | 2000 | 2.5 m/s | 23 m/s | 9 | 95% | 6.3 |
| Voorbeeld 1 | 6800 | 11.4 m/s | 46.2 m/s | 4 | 96.7% | 3.3 |
| Voorbeeld 2 | 29200 | 41 m/s | 46.2 m/s | 1.1 | 99.5% | 0.43 |

The invention claimed is:

1. Process for preparing caprolactam by admixture of cyclohexanone oxime to a reaction mixture comprising caprolactam and sulfuric acid using a mixing device, said mixing device comprising (i) a tube through which the reaction mixture can flow, and (ii) channels disposed around the tube, said channels opening into the tube, said process comprising: passing the reaction mixture through the tube, and feeding the cyclohexanone oxime into the reaction mixture through one or more of said channels, wherein Re>5000, Re being the Reynolds number as defined by ρ·V·D/η, wherein ρ=density (in kg/m³) of the reaction mixture that is fed to the tube V=velocity of the reaction mixture, V being defined as W/A, wherein W is the flow rate (in m³/s) of the reaction mixture that is fed into the tube and A is the cross section area of the tube (in m²) at the level where said channels open into the tube D=diameter of the tube at the level where said channels open into the tube (in m)

η=viscosity of the reaction mixture that is fed into the tube (in Pa·s).

2. Process according to claim 1, wherein Re>10.000.

3. Process according to claim 1, wherein the ratio w/W<0.05, wherein w=flow rate (in m³/s) of the cyclohexanone oxime which is fed into the reaction mixture through said one ore more channels, and W=flow rate (in m³/s) of the reaction mixture which is passed through the tube.

4. Process according to claim 1, wherein the ratio v/V is between 0.1 and 20, wherein v=the velocity (in m/s) at which cyclohexanone oxime is fed into the reaction mixture, V=velocity of the reaction mixture at the level where said channels open into the tube, V being defined as W/A, wherein W is the flow rate (in m³/s) of the reaction mixture that is fed into the tube and A is the cross section area of the tube (in m²) at the level where said channels open into the tube.

5. Process according to claim 4, wherein v/V is between 0.2 and 1.8.

6. Process according to claim 1, wherein the mixing device comprises one or more closures, one or more of the channels being closable with a closure, and wherein the process comprises selecting v/V by adjusting the number of channels that are closed with said closures.

7. Process according to claim 1, wherein the tube, as seen in the direction of flow, narrows, in a first part, to a throat, and which tube, optionally, widens beyond the throat in a second part.

8. Process according to claim 1, wherein a circulation system is provided, said circulation system comprising (i) the mixing device, (ii) a cooler for cooling the reaction mixture, (iii) a connecting circuit through which the reaction mixture can flow from the mixing device to the cooler, and from the cooler back to the mixing device and (iv) a pump for keeping the reaction mixture in circulation, wherein said pump is downstream of the mixing device and upstream of the cooler, as seen in the direction of flow of the reaction mixture; and wherein the process comprises circulating the reaction mixture from the mixing device to the cooler and from the cooler back to the mixing device.

9. Process according to claim 1, wherein the process comprises collecting the reaction mixture leaving the tube in a collecting vessel.

10. Process according to claim 9, wherein the mixing device comprises adjustable closures, and wherein the tube is conducted through the wall of the collecting vessel at a point downstream of the closures as seen in the direction of flow of the reaction mixture.

11. Process according to claim 1, wherein the ratio M defined as $(n_{so3}+n_{H2SO4})/n_{cap}$ is between 1 and 2.2, wherein
$n_{SO3}$=quantity of $SO_3$ in reaction mixture, in mol
$n_{H2SO4}$=quantity of $H_2SO_4$ in reaction mixture, in mol
$n_{cap}$=quantity of caprolactam in reaction mixture, in mol.

12. Process according to claim 1, wherein the reaction mixture comprises $SO_3$.

13. Process according to claim 12, wherein the $SO_3$ content in the reaction mixture is at least 2 wt. %.

14. Process according to claim 1, wherein the temperature of the reaction mixture is between 50 and 130° C.

* * * * *